(12) United States Patent
Griffiths (10) Patent No.: US 7,771,439 B2
(45) Date of Patent: Aug. 10, 2010

(54) GASTRIC BAND INSERTION INSTRUMENT

(75) Inventor: Jerry R. Griffiths, Pembroke, MA (US)

(73) Assignee: Symmetry Medical New Bedford Inc, New Bedford, MA (US)

( * ) Notice: Subject to any disclaimer, the term of this patent is extended or adjusted under 35 U.S.C. 154(b) by 999 days.

(21) Appl. No.: 11/315,714

(22) Filed: Dec. 22, 2005

(65) Prior Publication Data

US 2006/0200175 A1    Sep. 7, 2006

Related U.S. Application Data

(60) Provisional application No. 60/670,111, filed on Apr. 11, 2005, provisional application No. 60/650,290, filed on Feb. 4, 2005, provisional application No. 60/650,284, filed on Feb. 4, 2005.

(51) Int. Cl.
| | |
|---|---|
| *A61B 17/10* | (2006.01) |
| *A61B 17/12* | (2006.01) |
| *A61B 17/08* | (2006.01) |
| *A61B 17/00* | (2006.01) |
| *A61B 17/50* | (2006.01) |
| *A61F 11/00* | (2006.01) |
| *A61F 2/00* | (2006.01) |
| *A61F 2/02* | (2006.01) |

(52) U.S. Cl. ..................... 606/139; 606/157; 600/31; 600/37

(58) Field of Classification Search ................. 606/139, 606/140, 205–210, 141, 144, 151, 157, 228, 606/108; 600/37, 29, 30, 31
See application file for complete search history.

(56) References Cited

U.S. PATENT DOCUMENTS

| | | | | |
|---|---|---|---|---|
| 5,601,604 | A * | 2/1997 | Vincent | 606/216 |
| 7,144,400 | B2 * | 12/2006 | Byrum et al. | 606/140 |
| 2002/0029006 | A1 * | 3/2002 | Turturro et al. | 600/562 |
| 2003/0120285 | A1 * | 6/2003 | Kortenbach | 606/139 |
| 2004/0049207 | A1 * | 3/2004 | Goldfarb et al. | 606/139 |
| 2004/0204718 | A1 * | 10/2004 | Hoffman | 606/108 |

* cited by examiner

*Primary Examiner*—Darwin P Erezo
*Assistant Examiner*—Jing Ou
(74) *Attorney, Agent, or Firm*—AKC Patents LLC; Aliki K. Collins (57) ABSTRACT

An endoscopic surgical instrument is used in minimally invasive laparoscopic surgery for inserting a gastric band into a patient's abdomen through a laparoscopic port. The gastric band insertion instrument includes a handle, an elongated shaft and a distal end assembly. The elongated shaft includes an actuator rod that opens and closes a movable jaw at the distal end. A pin at the distal end assembly engages a hole in the front of the gastric band, and the movable jaw is closed thereby securely capturing the front end of the gastric band. The shaft and the captured gastric band are inserted through a laparoscopic port into the patient's abdomen.

8 Claims, 14 Drawing Sheets

GASTRIC BAND INSERTION INSTRUMENT

CROSS REFERENCE TO RELATED APPLICATIONS

This application claims the benefit of U.S. provisional application Ser. No. 60/670,111 filed on Apr. 11, 2005 and entitled GASTRIC BAND INSERTION INSTRUMENT which is commonly assigned and the contents of which are expressly incorporated herein by reference.

This application is also related to U.S. provisional application Ser. No. 60/650,290 filed on Feb. 4, 2005 and entitled SURGICAL ROTARY CAPTURE INSTRUMENT FOR GASTRIC BAND CLOSING which is commonly assigned and the contents of which are expressly incorporated herein by reference.

This application is also related to U.S. provisional application Ser. No. 60/650,284 filed on Feb. 4, 2005 and entitled SURGICAL HOOK INSTRUMENT FOR GASTRIC BAND CLOSING which is commonly assigned and the contents of which are expressly incorporated herein by reference.

FIELD OF THE INVENTION

The present invention relates to an endoscopic surgical instrument, and more particularly to a surgical instrument used in minimally invasive laparoscopic surgery for inserting a gastric band into a patient's abdomen through a laparoscopic port.

BACKGROUND OF THE INVENTION

Figure 1:
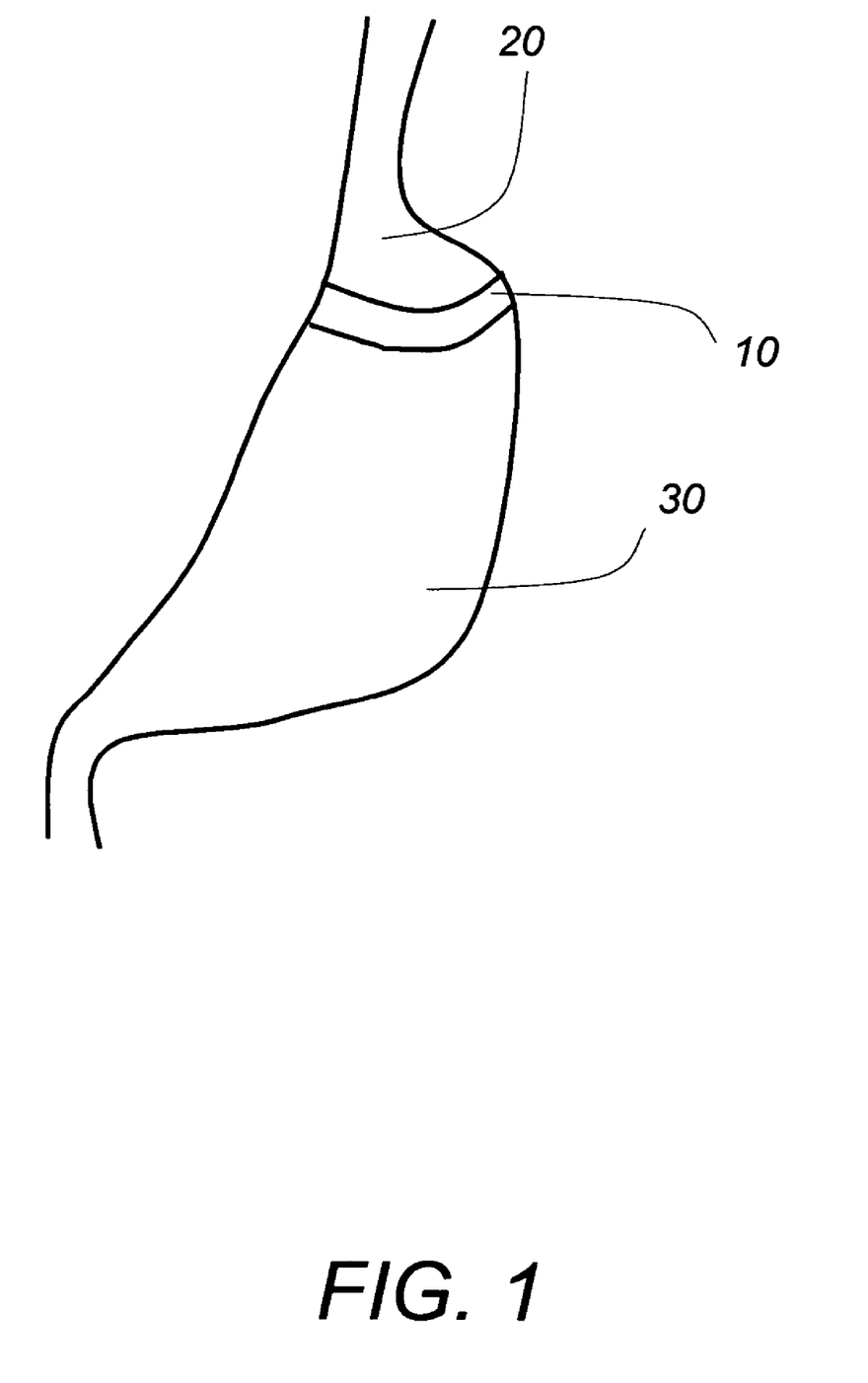
FIG. 1 is a side view of a stomach with the an adjustable gastric band around the upper part of the stomach.

One method of controlling the intake of food in an obese person is to place an adjustable restriction band 10 around the upper stomach 20, shown in FIG. 1. This creates a new small stomach pouch in the upper stomach 20 for holding a small amount of food and leaves the larger part of the stomach below the band so the stomach volume available for holding food is reduced. The band also controls the stoma, i.e., stomach outlet, between the upper stomach and the lower stomach 30. The size of the stoma regulates the flow of food from the upper stomach to the lower stomach. When the stoma is small the patient feels full sooner and has a feeling of satiety that lasts longer.

Figure 2A:
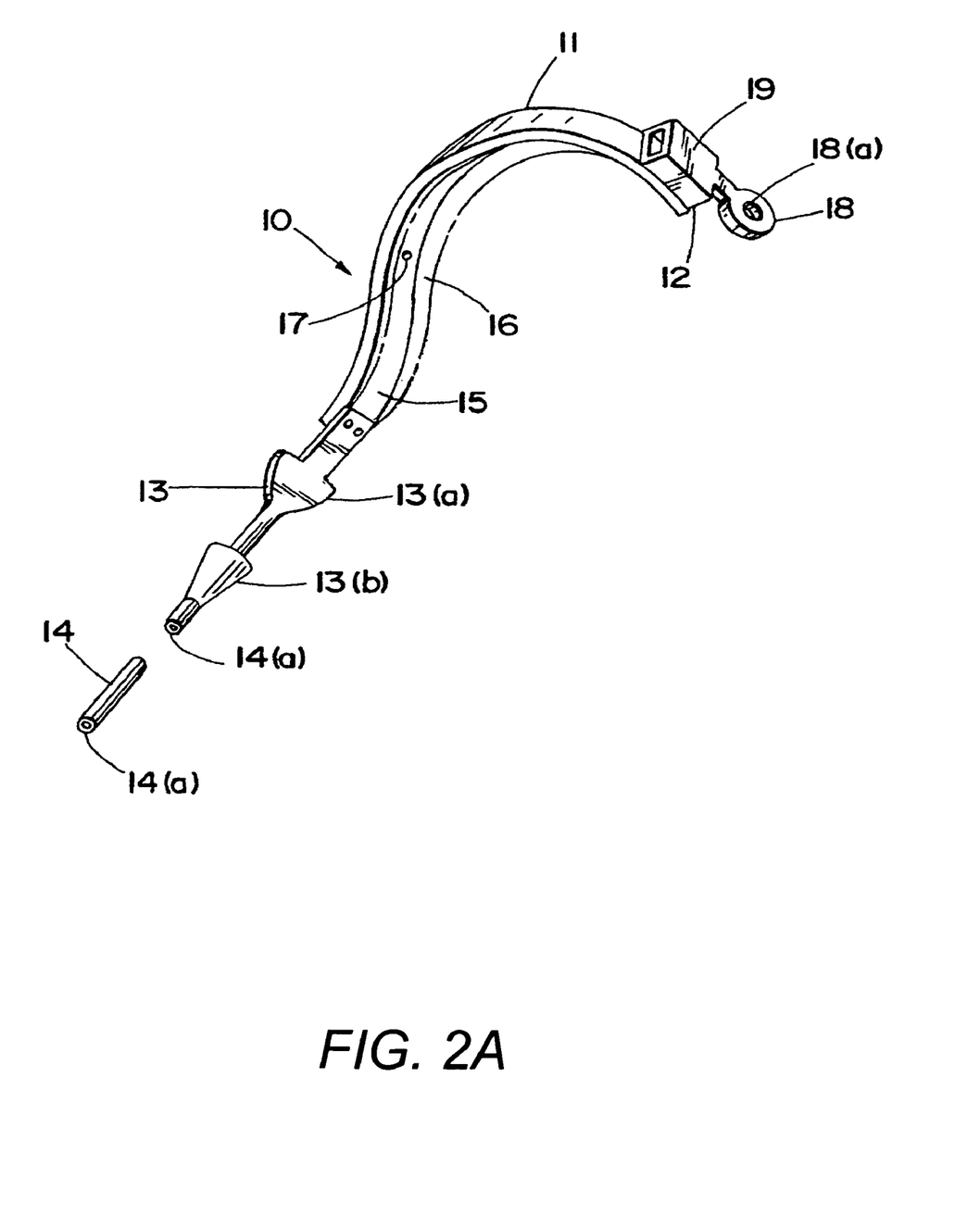
FIG. 2A is a perspective view of an open LAP-BAND gastric band.
Figure 2B:
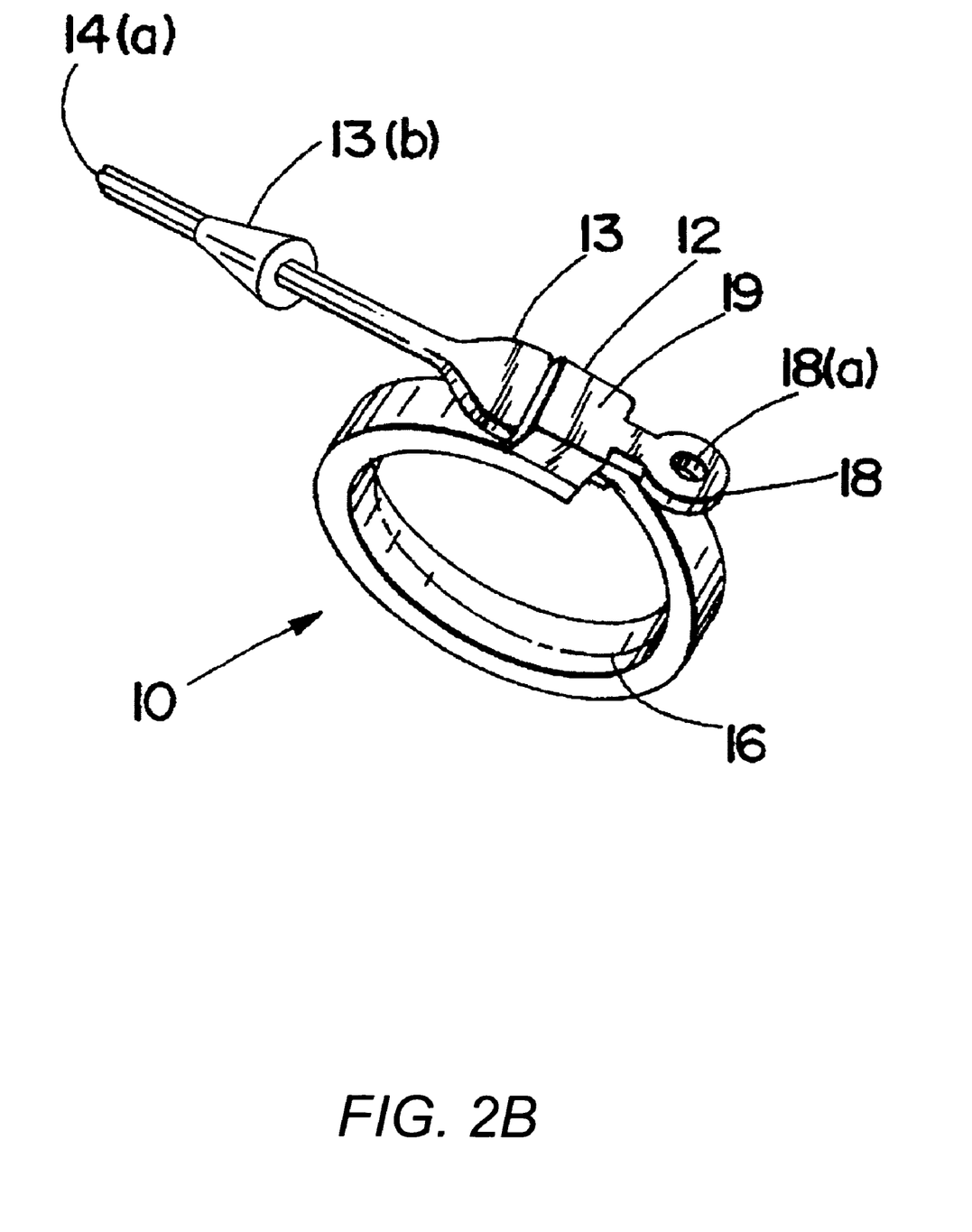
FIG. 2B is the gastric band of FIG. 2A in a closed position forming a ring structure.

One specific type of an adjustable restriction band 10 is the LAP-BAND system manufactured by INAMED Corporation, shown in FIG. 2A and FIG. 2B. The LAP-BAND system is described in U.S. Pat. No. 5,601,604, the contents of which are incorporated herein by reference. Referring to FIG. 2A, the gastric band 10 of the LAP-BAND system includes a body portion 11 a head portion 12 and a tail portion 13. The head portion 12 has a buckle 19 with a pull tab 18 and the pull tab 18 has a hole 18a for receiving a post. The tail portion 13 has a tube 14 extending from one end, a triangular shaped member 13a and a conical shaped barb 13b. Tube 14 is in communication with an inflatable member 16 of the inner surface 15 of the body portion 11. The inflatable member 16 is gradually inflated by injecting a saline solution through the tube 14. The inflated member 16 presses against and constricts the stomach wall underlying the band 10. This results in decreasing the diameter of the stoma. The amount of the injected solution controls the size of the inflated member 16 and accordingly the diameter of the stoma.

During a minimally invasive laparoscopic surgical procedure, the tube 14 of the gastric band 10 is pushed through a laparoscopic cannula and is inserted in the patient's abdomen. The gastric band 10 is then placed around the patient's upper stomach and the tail portion 13 is inserted into the buckle 19 thereby forming a ring structure around the upper stomach. The triangular shaped member 13a of the tail portion 13 interlocks with the buckle 19 and prevents the tube 14 from slipping backwards.

Minimally invasive tools are used for inserting the gastric band into the patient's abdomen and for performing the mechanical manipulations needed for tightening the gastric band around the upper stomach. Surgeons performing this type of laparoscopic surgery have encountered the problem of the gastric band unintentionally disengaging from the insertion tool during insertion. This requires regrasping the tab 18 several times during the insertion procedure, which increases both the operation time and the complexity of the operation.

Accordingly there is a need for an improved minimally invasive tool used for inserting the gastric band through a laparoscopic port into the patient's abdomen that prevents unintentional disengaging.

SUMMARY OF THE INVENTION

The present invention provides a surgical instrument used in minimally invasive laparoscopic surgery for inserting a gastric band into a patient's abdomen through a laparoscopic port that prevents unintentional disengagement of the gastric band.

In general, in one aspect, the invention features an endoscopic surgical insertion tool used in minimally invasive surgery for capturing and inserting an elongated strap into a patient's body. The elongated strap has a pull tab at one end. The insertion tool includes an elongated shaft having a longitudinal axis, a handle at a proximal end and an end assembly at a distal end. The end assembly is configured to engage a hole in the pull tab and securely capture the pull tab and then the elongated shaft is used to push the pull tab and thereby the elongated strap into the patient's body.

Implementations of this aspect of the invention may include one or more of the following features. The end assembly comprises a flat member having a first end attached to the distal end of the elongated shaft, a rounded cone-shaped nose extending from a second end of the flat member, and a movable jaw articulately connected to the second end. The flat member further comprises a top surface having a pin projecting from it. The pin is configured to first engage the hole in the pull tab and then the movable jaw is configured to close downward over the pin, and thereby securely capturing the pull tab between the pin and the closed movable jaw. The elongated shaft comprises a hollow tube and the hollow tube encloses an actuator rod configured to move back and forth along the longitudinal axis. The actuator rod is connected to the movable jaw and is configured to actuate the movable jaw through the back and forth motion. The handle comprises a collar configured to slide back and forth along the handle and thereby to move the actuator rod back and forth along the longitudinal axis. The handle is configured to provide tactile control of the movable jaw orientation. The handle comprises a cylindrical body having first and second side indentations opposite to each other and a thumb indentation on a top surface of the cylindrical body. The thumb indentation is aligned with the movable jaw. The elongated shaft is inserted into the patient's body through a cannula and the shaft is dimensioned to enter one end, pass through and extend beyond the other end of the cannula. The rounded cone-shaped nose is configured to open seals and gates in a port of the cannula. The elongated strap comprises a ligature band having a buckle end and a distal end, the buckle end having an aperture and the pull tab. The elongated strap is configured to encircle an internal organ and the distal end is configured to pass through and lockingly engage the aperture thereby tightening the ligature band around the internal organ.

In general, in another aspect, the invention features a method for inserting an elongated strap via minimally invasive surgery into a patient's body. The method includes the following steps. First providing an elongated strap having a pull tab at one end. Then providing an elongated shaft having a longitudinal axis, a handle at a proximal end and an end assembly at a distal end. Then engaging a hole in the pull tab with the end assembly and securely capturing the pull tab. Then inserting the elongated shaft with the captured elongated strap into the patient's body and pushing the pull tab and thereby the elongated strap into the patient's body.

Among the advantages of this invention may be one or more of the following. The movable jaw and the pin of the end assembly engage and securely capture the pull tab. The risk of unintentional disengagement is very low.

The details of one or more embodiments of the invention are set forth in the accompanying drawings and description below. Other features, objects and advantages of the invention will be apparent from the following description of the preferred embodiments, the drawings and from the claims.

BRIEF DESCRIPTION OF THE DRAWINGS

Referring to the figures, wherein like numerals represent like parts throughout the several views.

DETAILED DESCRIPTION OF THE INVENTION

Figure 3:
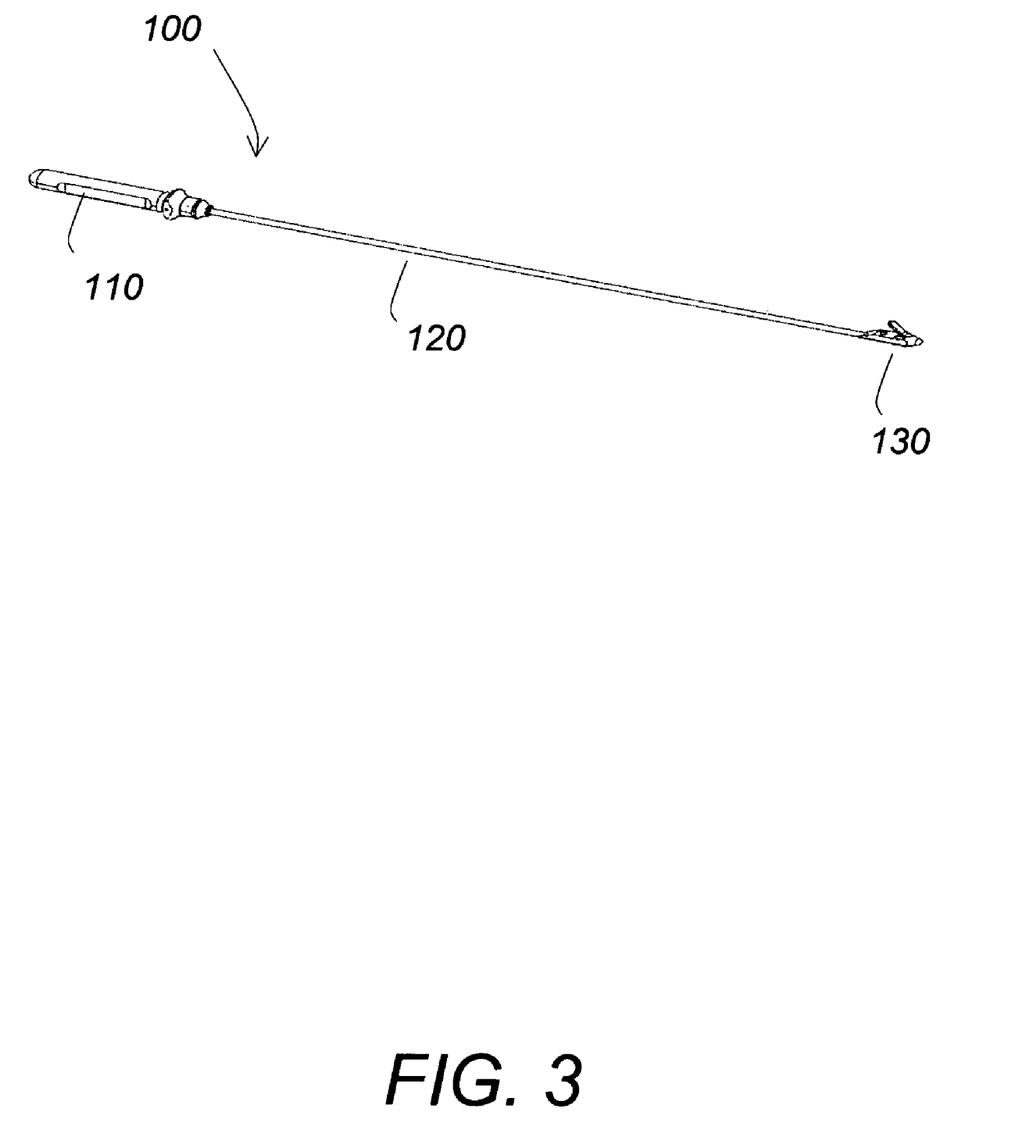
FIG. 3 is a perspective view of the endoscopic insertion instrument of this invention.
Figure 7:
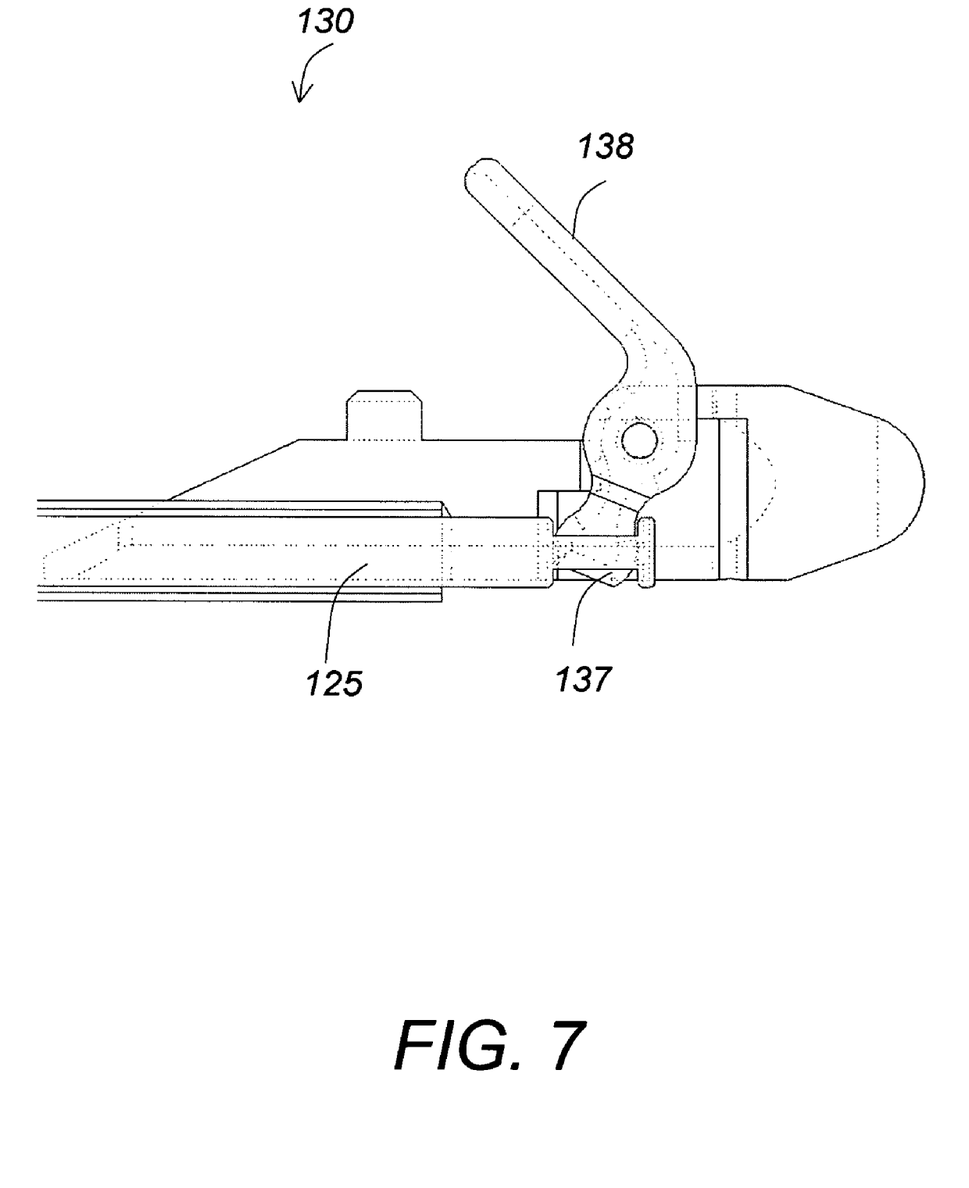
FIG. 7 is a cross-sectional side view of the distal end of the instrument of FIG. 3 in the open position.
Figure 8:
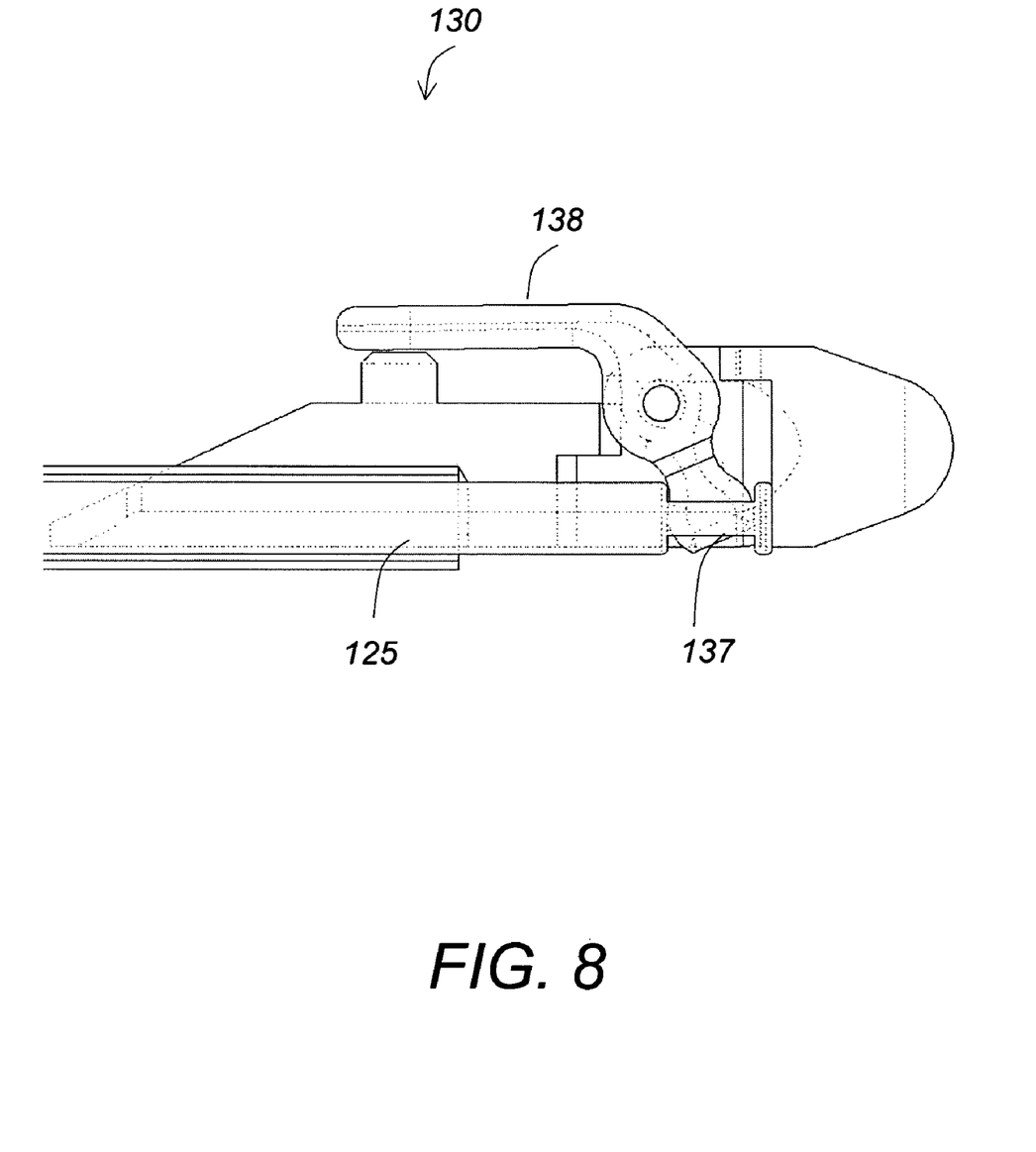
FIG. 8 is a cross-sectional side view of the distal end of the instrument of FIG. 3 in the closed position.

Referring to FIG. 3, a gastric band insertion instrument 100 includes a handle 110, an elongated shaft 120 and a distal end assembly 130. The handle 110 provides control of the distal end assembly 130 via an actuator rod 125, shown in FIG. 7.

Figure 4:
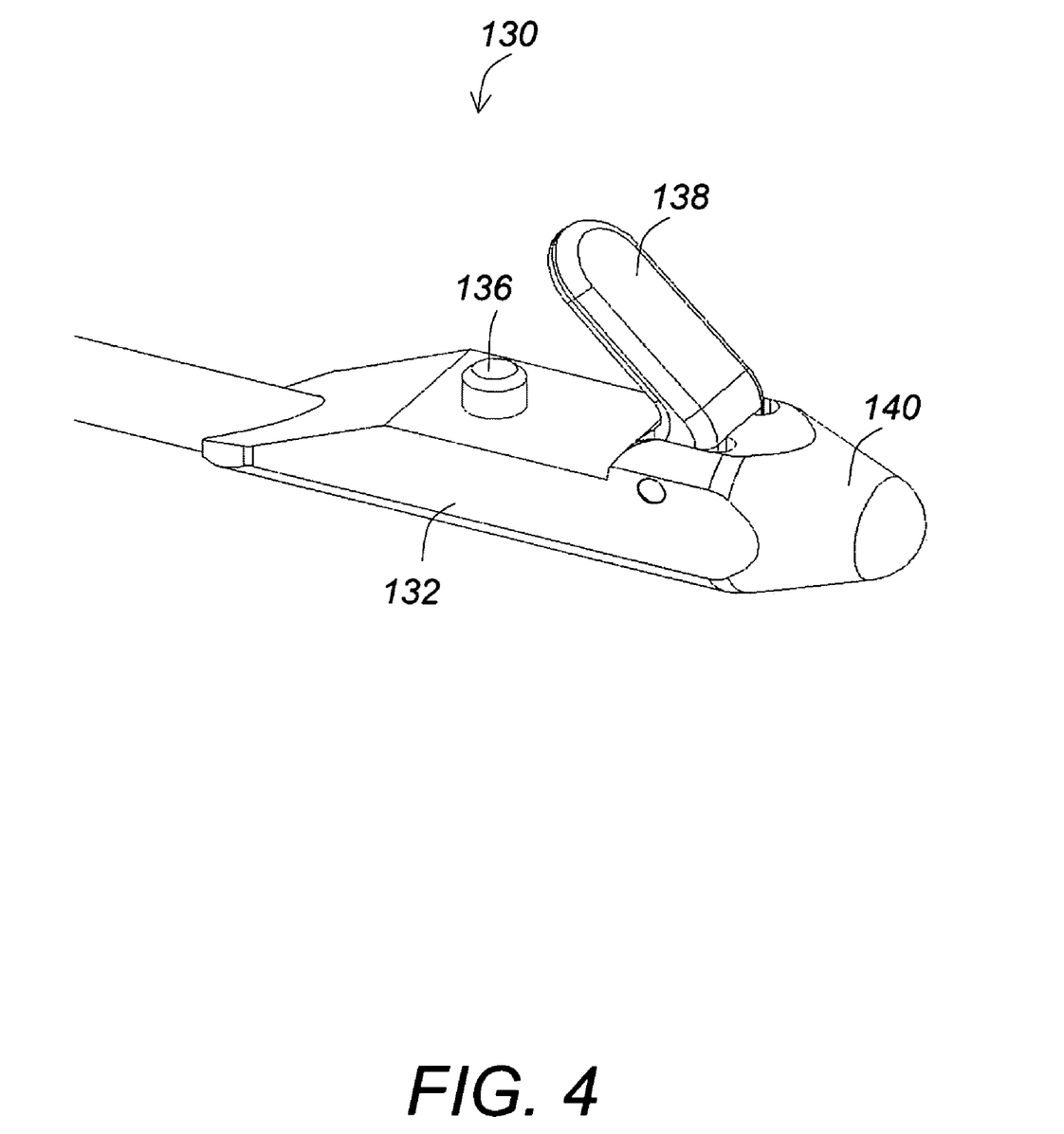
FIG. 4 is a perspective view of the distal end assembly of the instrument of FIG. 3.
Figure 5:
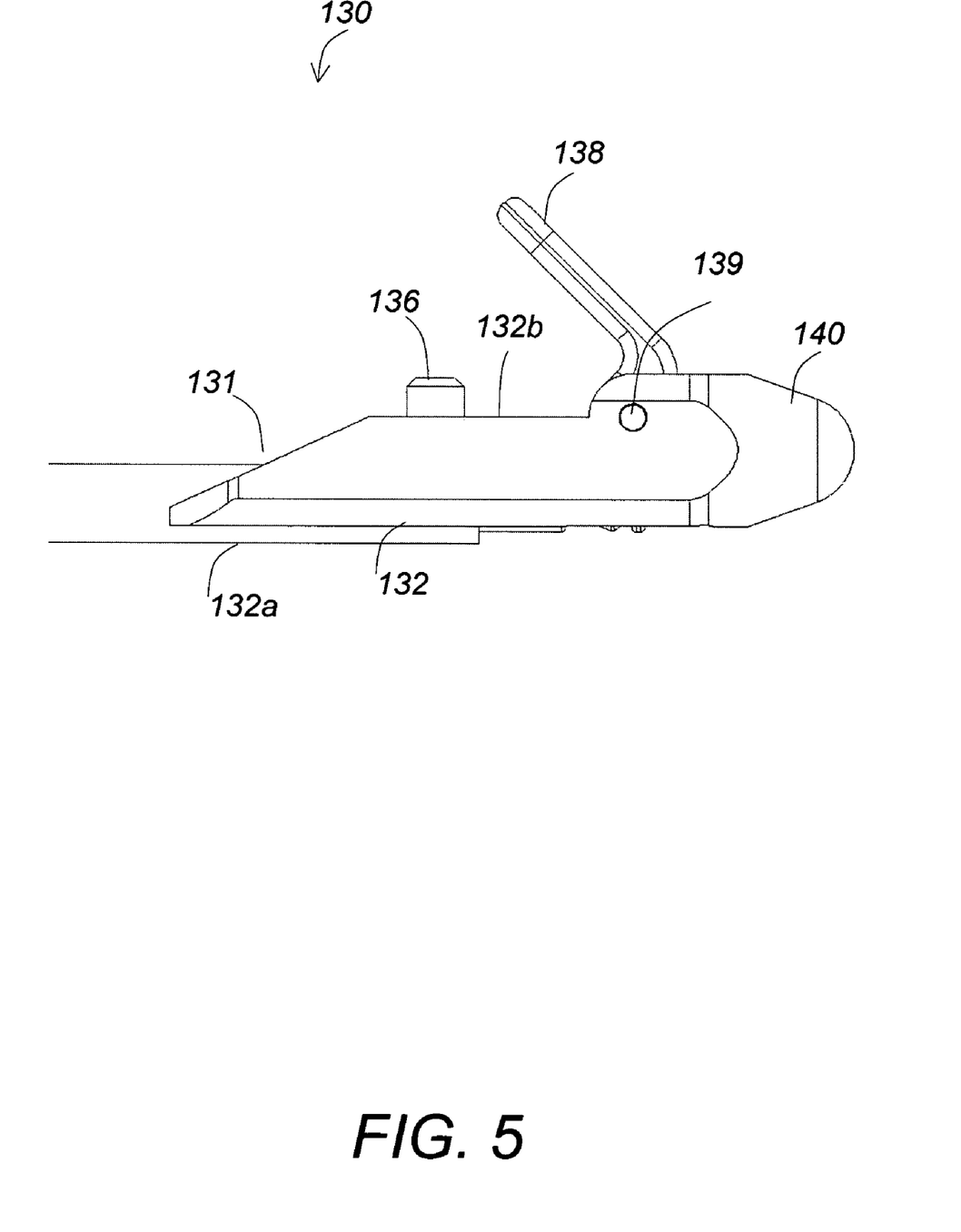
FIG. 5 is a side view of the distal end assembly of the instrument of FIG. 3 in the open position.
Figure 6:
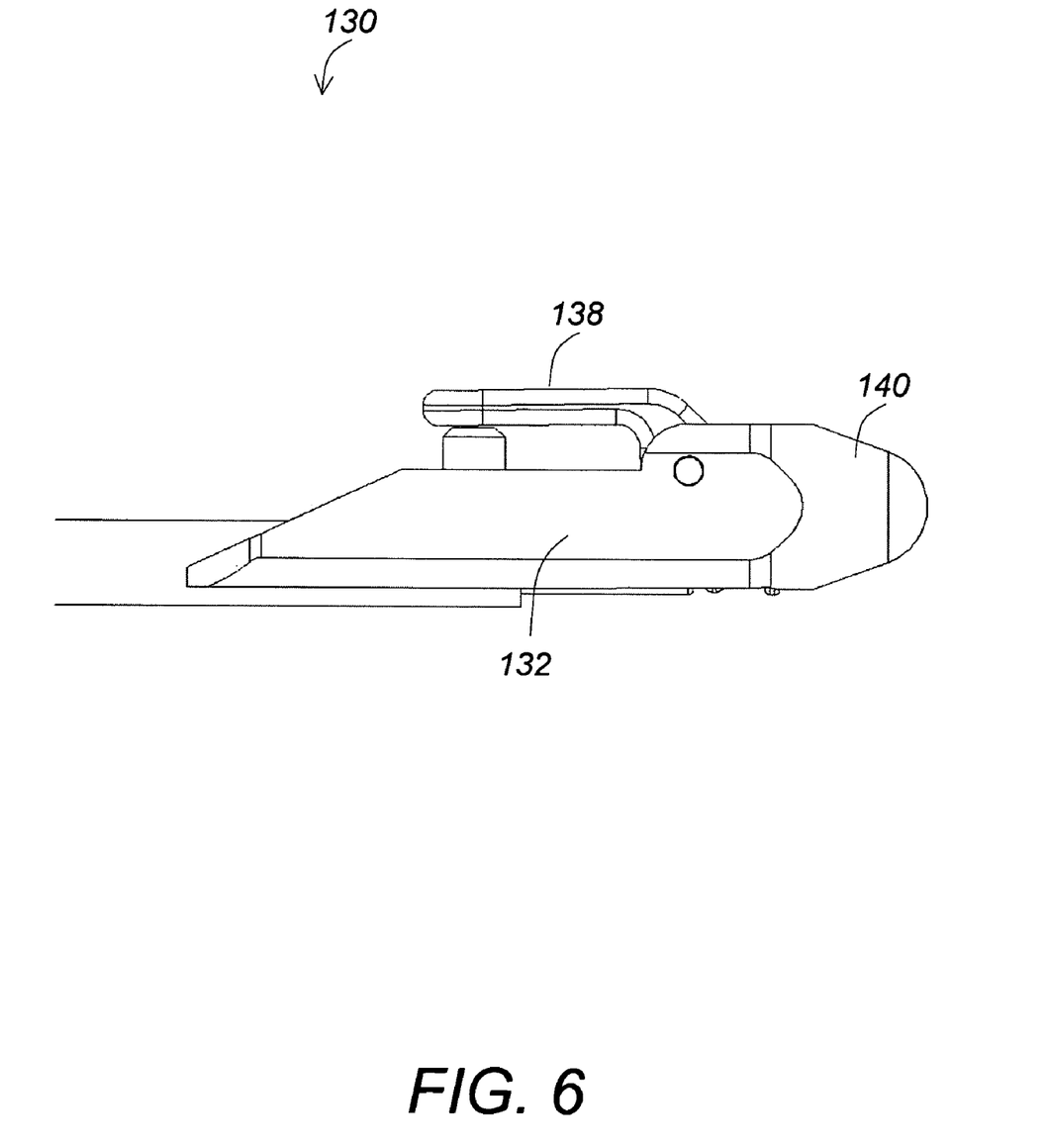
FIG. 6 is a side view of the distal end assembly of the instrument of FIG. 3 in the closed position.
Figure 9:
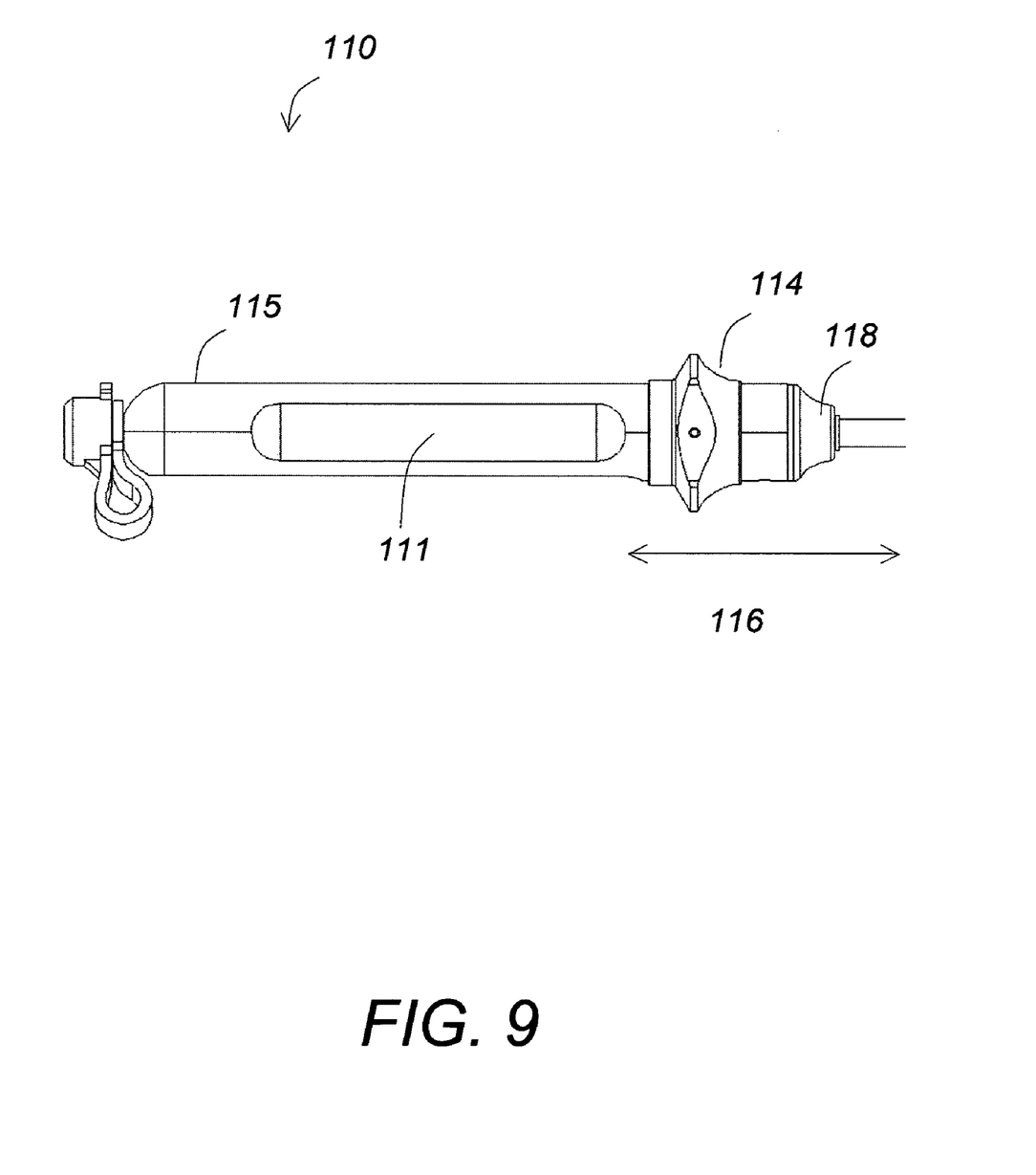
FIG. 9 is a side view of the handle of the instrument of FIG. 3.
Figure 10:
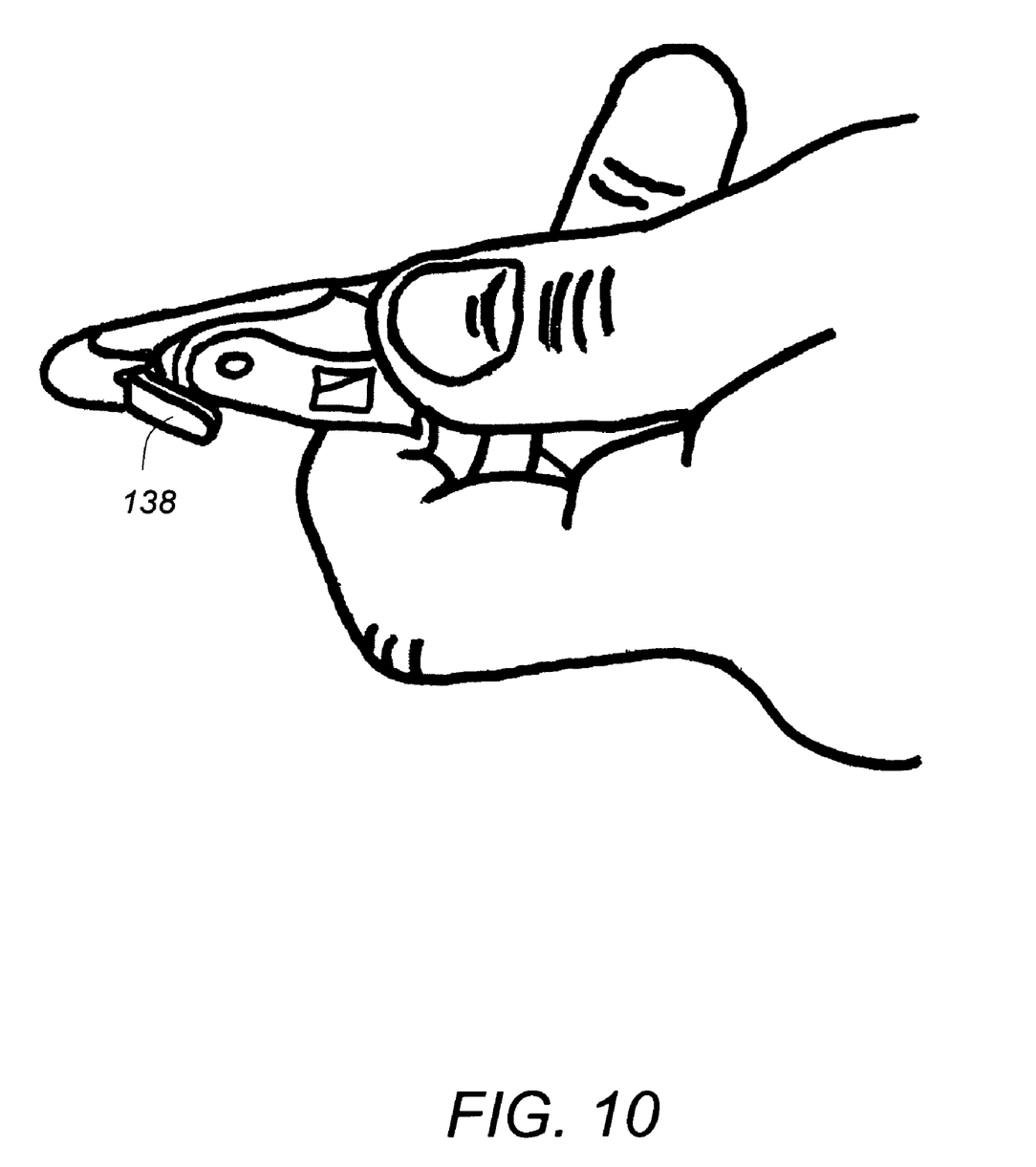
FIG. 10 depicts the distal end of the instrument of FIG. 3 engaging the hole in the tab of the buckle of the gastric band of FIG. 2A.

Referring to FIG. 9 the handle 110 features a cylindrical body 115 having a diameter of 15.9 mm and a length of 11.4 cm and it includes two side indentations 111, 112 (not shown) opposite to each other and a thumb indentation 113 (not shown) on the top surface. The thumb indentation 113 is aligned with the orientation of a movable jaw element 138, shown in FIG. 4. The handle 110 also features a flared collar 114 that slides back and forth along the direction 116 in order to move the actuator 125, shown in FIG. 7, that controls the movement of the movable jaw element 138 (shown in FIG. 7) of the distal end assembly 130.

Figure 11:
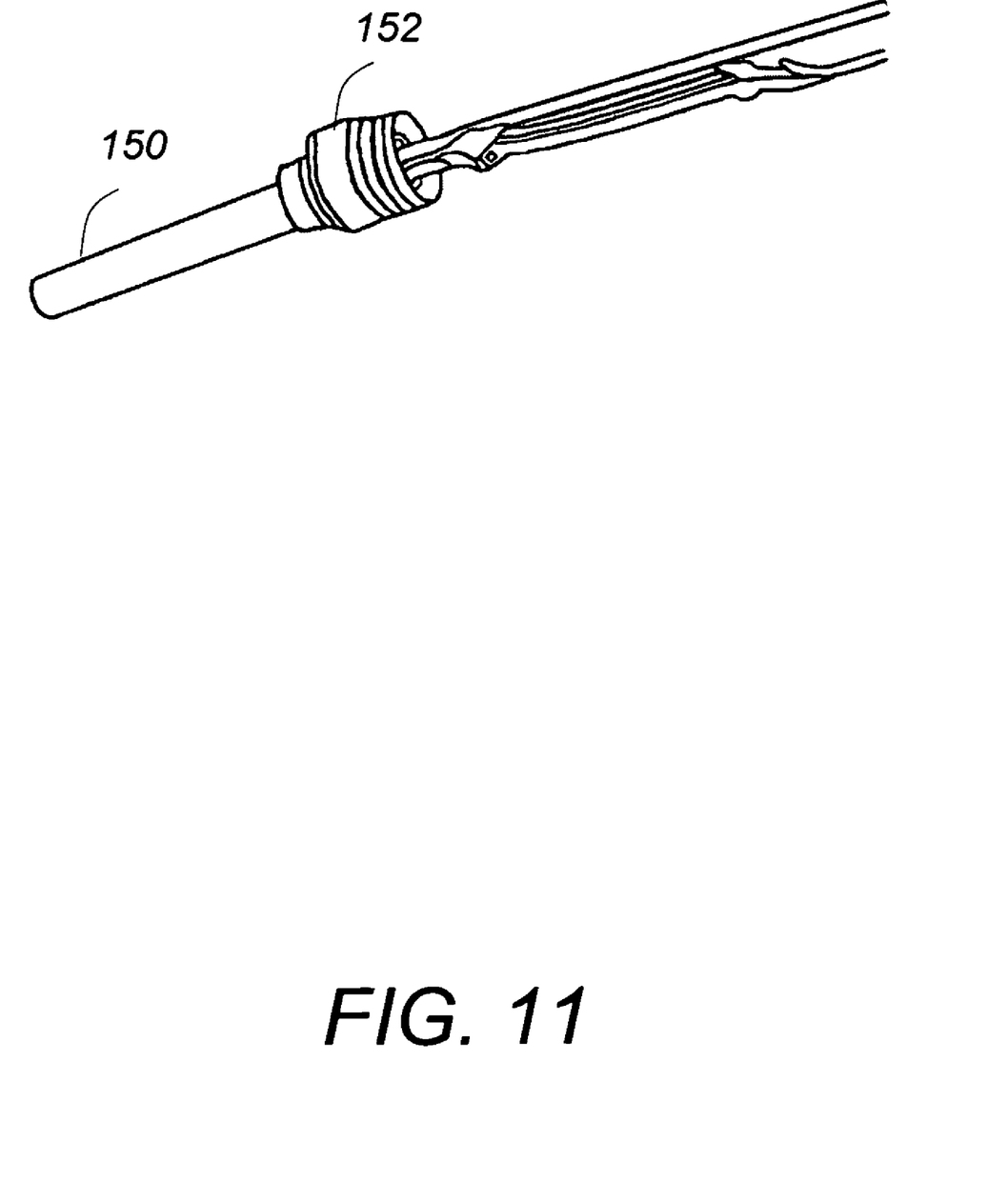
FIG. 11 depicts the insertion of the gastric band of FIG. 2A through an insertion port and through the front end of the laparoscopic cannula.
Figure 12:
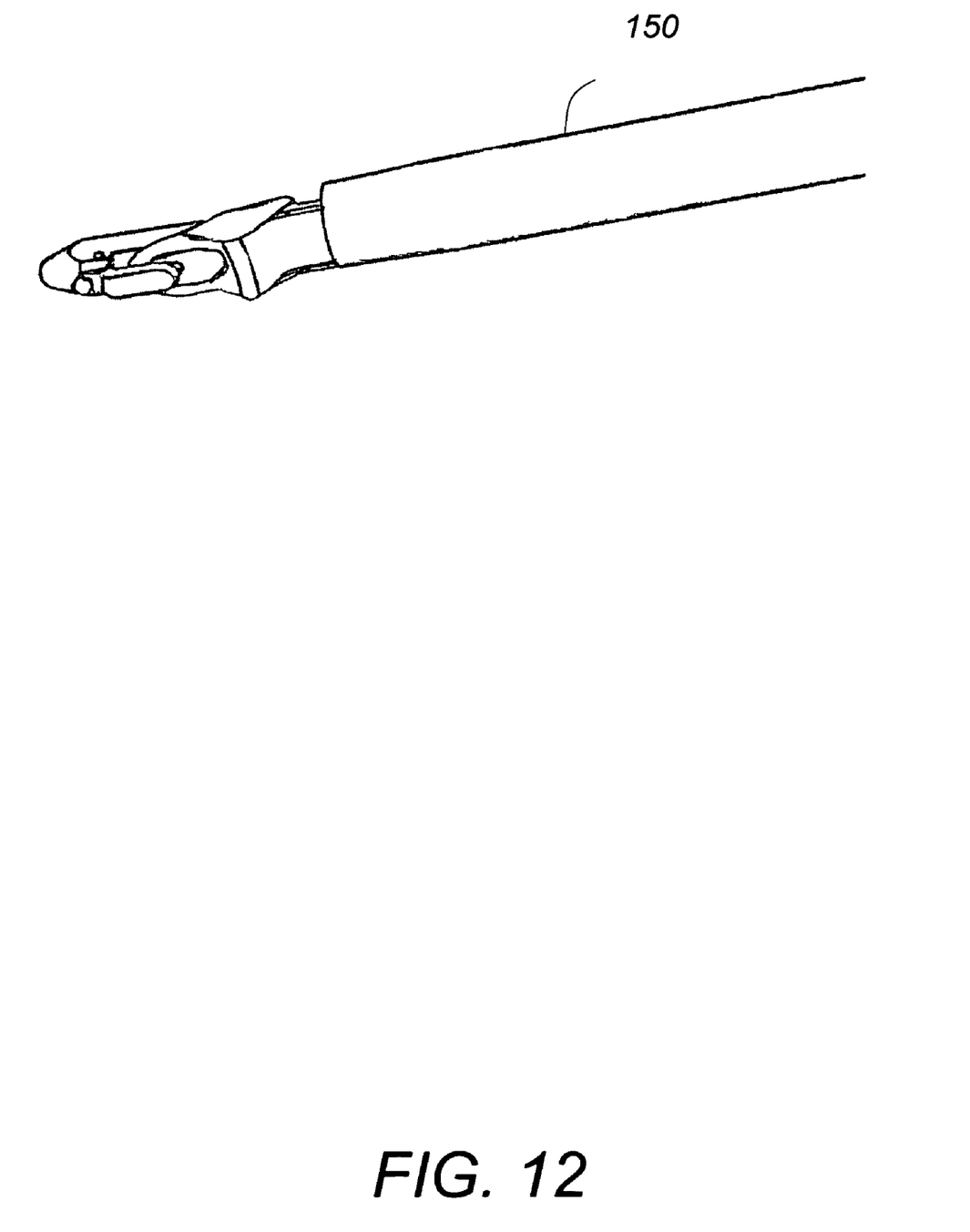
FIG. 12 depicts the gastric band of FIG. 2A and the front end assembly of the insertion instrument of FIG. 3 as they emerge from the laparoscopic cannula.
Figure 13:
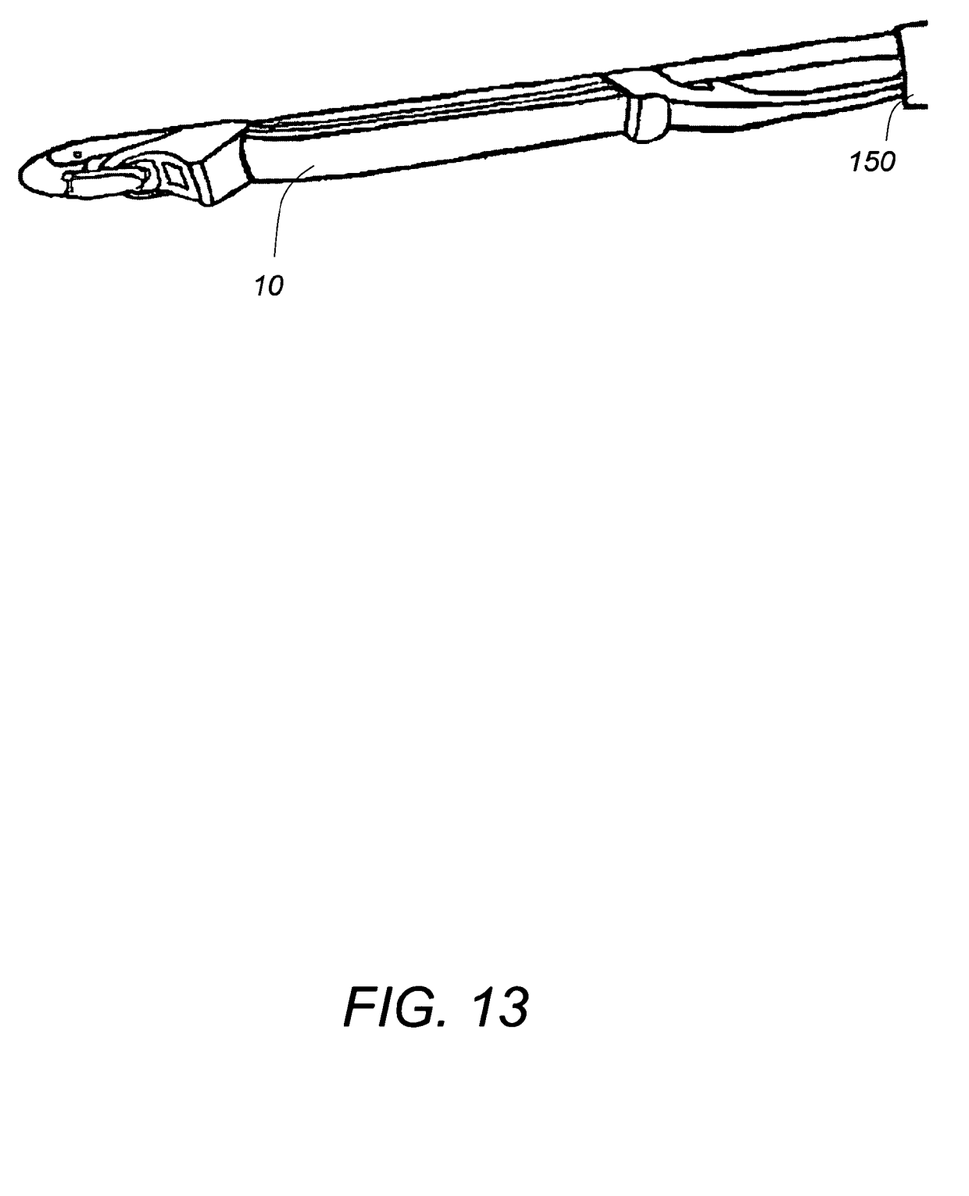
FIG. 13 shows the distal end of the instrument of FIG. 3 securely holding the tab of the buckle of the gastric band of FIG. 2A as it exits the laparoscopic cannula.

The elongated shaft 120 has a cylindrical shape and is dimensioned to fit through a laparoscopic cannula 150, shown in FIG. 11 and FIG. 12, for minimally invasive surgery. In one example, the elongated shaft 120 has a length of 45 cm and a diameter of 5 mm. The elongated shaft 120 is hollow inside, forming a tube that encloses the above mentioned actuator rod 125, shown in FIG. 7. The actuator rod 125 engages a slot 137 in the bottom of the above mentioned movable jaw 138 (also shown in FIG. 7).

Referring to FIGS. 4-8, the distal end 130 includes a flat portion 132, a movable jaw 138 and a rounded cone shaped nose 140. The flat portion 132 has a top surface 132a and a bottom surface 132b. The top surface 132a includes an angled portion 131 and a pin 136 projecting from it. The pin 136 engages the hole 18a of the tab 18 and the movable jaw 138 is spring-loaded to the closed position and closes downward over the pin to securely capture the tab 18. Once the gastric band is securely captured by the closed jaw 138, the gastric band 10 is stretched out along the length of the shaft 120 and the tubing is pulled slightly to keep the band stretched. Ahead of the jaw pivot 139 is the rounded cone shaped nose 140 that is used to smoothly open the seals and gates of the port 152 as it is pushed through, shown in FIG. 11. Once the gastric band 10 is completely through the cannula 150 and at the release site, the handle collar 114 is actuated again, and the movable jaw 138 opens, releasing the pull tab 18. The natural tendency of the band 10 to curl up causes the tab 18 to disengage from the pin 136. The collar 114 is released and the movable jaw 138 is closed. The inserter 100 is then retracted back through the cannula 150. A capped luer connector 118, shown in FIG. 9, at the end of the handle 110 is available for flushing the instrument clean prior to sterilization. The insertion process may be performed under optical or fluoroscopic visualization.

Other embodiments may include one or more of the following. The insertion instrument 100 may be inserted directly through the incision, without the need to use a laparoscopic cannula 150. The rounded cone shaped nose 140 helps direct the instrument through the skin, fascia and muscle layers.

Several embodiments of the present invention have been described. Nevertheless, it will be understood that various modifications may be made without departing from the spirit and scope of the invention. Accordingly, other embodiments are within the scope of the following claims.

What is claimed is:

1. An endoscopic surgical system used in minimally invasive surgery for capturing and pushing an elongated strap, said system comprising:

an elongated shaft extending along a longitudinal axis, a handle attached to a proximal end of said elongated shaft and an end assembly attached to a distal end of said elongated shaft;

wherein said end assembly comprises a flat member extending along said longitudinal axis and comprising a first end attached to said distal end of said elongated shaft and a rounded cone-shaped second end, and a movable jaw articulately connected to said second end of said flat member;

an elongated strap comprising a buckle end and a distal end, said buckle end comprising an aperture and a pull tab;

wherein said end assembly is configured to engage a hole in said pull tab and securely capture said pull tab and whereupon said elongated shaft is used to push said pull tab and thereby said elongated strap; and wherein said elongated strap is configured to encircle an internal organ and said elongated strap distal end is configured to pass through and lockingly engage said aperture thereby tightening said elongated strap around said internal organ.

2. The endoscopic surgical system of claim 1 wherein said flat member further comprises a top surface having a pin projecting from it and wherein said pin is configured to be inserted into said pull tab hole and then said movable jaw is configured to be closed downward over said pin, and thereby said pull tab is securely captured between said pin and said closed movable jaw.

3. The endoscopic surgical system of claim 2 wherein said elongated shaft comprises a hollow tube and said hollow tube encloses an actuator rod configured to move back and forth along said longitudinal axis, and wherein said actuator rod is connected to said movable jaw and is configured to actuate said movable jaw through said back and forth motion.

4. The endoscopic surgical system of claim 3 wherein said handle comprises a collar configured to slide back and forth along said handle and thereby to move said actuator rod back and forth along said longitudinal axis.

5. The endoscopic surgical system of claim 2 wherein said handle is configured to provide tactile control of said movable jaw orientation.

6. The endoscopic surgical system of claim 2 wherein said handle comprises a cylindrical body having first and second side indentations opposite to each other and a thumb indentation on a top surface of said cylindrical body, said thumb indentation being aligned with said movable jaw.

7. The endoscopic surgical system of claim 1 wherein said elongated shaft is inserted through a cannula and is dimensioned to enter one end, pass through and extend beyond the other end of said cannula.

8. The endoscopic surgical system of claim 7 wherein said rounded cone-shaped second end is configured to open seals and gates in a port of said cannula.

* * * * *